United States Patent [19]

Meivogel

[11] Plant 4,718

[45] May 19, 1981

[54] EVERGREEN AZALEA

[75] Inventor: Simon P. Meivogel, Perry, Ohio

[73] Assignee: The Cottage Gardens, Inc., Perry, Ohio

[21] Appl. No.: 96,472

[22] Filed: Nov. 21, 1979

[51] Int. Cl.[3] ..... A01H 5/00

[52] U.S. Cl. ..... Plt./57

[58] Field of Search ..... Plt./55-57

*Primary Examiner*—Robert E. Bagwill

*Attorney, Agent, or Firm*—Baldwin, Egan, Walling & Fetzer

[57] ABSTRACT

A hardy, evergreen azalea which is also suitable for forcing, having vivid pink blossoms and variegated foliage.

1 Drawing Figure

1

This invention comprises a new and distinct evergreen azalea. It is a result of an asexually propagated bud sport taken from the parent plant of Girard's Rose. Parent cross: (Fedora 33 El Capitan) × (Boudoir × Boudoir). Variegated foliage of glossy green leaves edged with creamy white margins characterizes this azalea's distinctiveness.

The sport was discovered by me, June, 1975, in a cultivated area at The Cottage Gardens, Inc., 4992 Middle Ridge Road, Perry, Ohio, at which time it was apparent that it had desirable qualities that should be preserved.

The novel variety was propagated by softwood cuttings June 1, 1975, with 100% rootability. These original rooted cuttings subsequently became the parent stock for early cutting material. Techniques were used to propagate the variegation for consistency. Consistent variegation has been obtained with a low percentage reverting back to the non-variegated parent plant. Some stock was propagated using hardwood cutting techniques in January, 1976, again with 100% rootability.

The hardiness was tested in zones five and six (reference—The Zones of Plant Hardiness U.S.D.A. Map) through the 1978–1979 winter season. The bitter winter dropped temperatures well below the expected range of minimum temperatures subsequently destroying all plants tested. However, the azalea is thought to be hardy to temperatures of at least 0 degrees Fahrenheit. If proper cultural practices such as mulching to insure winter insulation is considered, the plant should not suffer any serious winter damage. It has been suggested that this plant is ideal for an early season crop, (i.e. a forcing azalea).

The accompanying illustration shows a mass of plants in container production exhibiting a late season bloom engulfed with the uniquely shaped variegated foliage.

The following is a detailed description of the plant, color reference being to the Royal Horticultural Society Colour Chart—Revised Edition, 1966:

2

Foliage: The novelty of the foliage is in its deep green leaves edged with creamy white margins, (green; yellow-green 147A, white; greyed-yellow 160B). The summer leaves are high-lighted with a glossy sheen followed by a pinkish bronze fall colour, (i.e. green changing to brown 200A, white margins taking on pink tinges; red 37B). The shape of the foliage offers added interest because of its high degree of variability. Leaf tips are irregular acuminate. Leaves are borne in a flat to convex plane with sizes ranging from $1\frac{1}{2}$–2 inches long by $\frac{1}{2}$–$\frac{3}{4}$ inches wide.

Flowers: The flowers are of excellent substance offering a vivid pink bloom in mid-May, (petal color; red 53D). Individual flowers are openly funnel-shaped with five to seven connate lobes. The petals are frilled with wavy margins. Flower size is 2 inches wide by $1\frac{3}{4}$ inches long. Flowers may be borne alone or in a cluster of two to eight gracefully massing over the foliage. The floral clusters measure 2–5 inches wide. The pink stamens are curved, uneven in length, 5–7 in number. Anther colour is darker than the filament, (filament; red 53C, anther; greyed-purple 187D). The pistil is curved with stigma colour slightly darker than the style, (stigma; red 53D, style; red 53C). The ovary is tomentose, hypogynous with 5 completely united carpels. The calyx is $\frac{1}{8}$ inch to 3/16 inches long, fuzzy with tomentum. The expanding buds are deeper pink than the bloom.

Characteristics of growth: The growth habit is upright to broad with well developing branches. An average size of a three year old plant propagated by cuttings is 12–15 inches tall by 12–15 inches wide.

I claim:

1. The new and distinct variety of variegated evergreen azalea substantially as herein shown and described, characterized particularly by its unique variegated foliage, green leaves with white edges, which is different from any other known evergreen azalea.

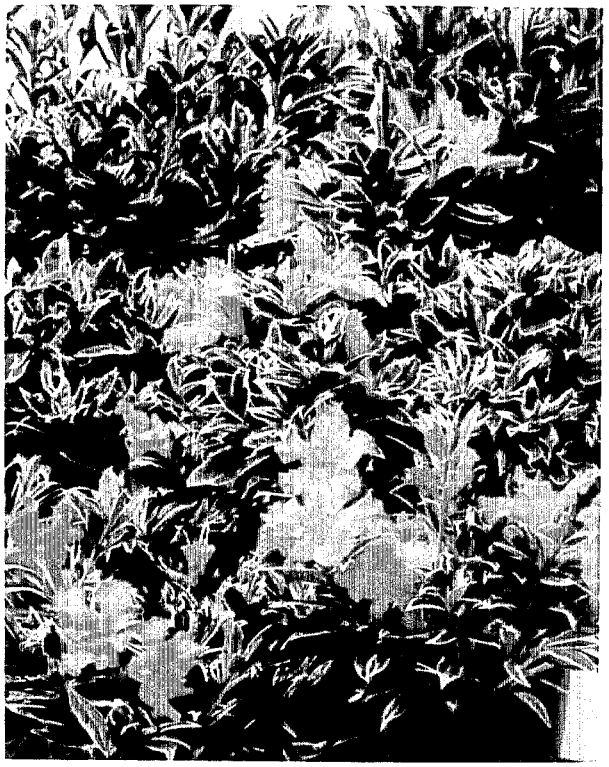

* * * * *